United States Patent [19]

Sanford et al.

[11] Patent Number: 5,225,160
[45] Date of Patent: Jul. 6, 1993

[54] MEDICAL INSTRUMENT DECONTAMINATION AND STERILIZATION PROCESSOR

[75] Inventors: Bill R. Sanford, Mentor; Raymond C. Kralovic, Austinburg, both of Ohio

[73] Assignee: Steris Corporation, Mentor, Ohio

[21] Appl. No.: 741,788

[22] Filed: Aug. 6, 1991

Related U.S. Application Data

[63] Continuation-in-part of Ser. No. 681,118, Apr. 5, 1991, and a continuation-in-part of Ser. No. 349,304, May 9, 1989, Pat. No. 5,091,343, which is a continuation-in-part of Ser. No. 140,388, Jan. 4, 1988, Pat. No. 4,892,706, and Ser. No. 165,189, Mar. 7, 1988, Pat. No. 5,037,623, said Ser. No. 681,118, is a continuation-in-part of Ser. No. 140,388, Mar. 7, 1988, and Ser. No. 165,189, Mar. 7, 1988, said Ser. No. 140,388, is a continuation-in-part of Ser. No. 826,730, Feb. 6, 1986, Pat. No. 4,731,222, said Ser. No. 165,189, is a continuation-in-part of Ser. No. 826,730, Feb. 6, 1986.

[51] Int. Cl.[5] .............................................. A61L 2/18
[52] U.S. Cl. ..................................... 422/28; 134/161; 134/199; 134/200; 422/1; 422/292; 422/297; 422/300
[58] Field of Search .................... 422/1, 28, 292, 297, 422/300; 134/161, 199, 200

[56] References Cited

U.S. PATENT DOCUMENTS 4,410,492 10/1983 Kaye .................................. 422/27
5,090,433 2/1992 Kamaga ......................... 134/200 X Primary Examiner—Jill A. Johnston
Attorney, Agent, or Firm—Fay, Sharpe, Beall, Fagan, Minnich & McKee

[57] ABSTRACT

An instrument (28) or other item to be sterilized is supported on a hanger (26) in a decontamination chamber (10). A container such as a sleeve (92), is supported at adjacent ends between supporting rings (90) such that the container surrounds and is displaced from the instrument. A pump (40) recirculates a sterilant or other antimicrobial solution that collects in a lower drain (48) and a reservoir (50) through spray nozzles (70, 96) and connectors (44) which are connected to interior passages of the instrument. In this manner, the internal passages of the instrument are sterilized by the flowing liquid and exterior surfaces are sterilized by sterilant solution mist which condenses on and coats the exterior surface. After the instrument is sterilized, a sterile rinse is sprayed on the instrument and interior of the container. The container and instrument are removed as a unit and the container is closed at its ends to prevent the instrument from becoming microbially contaminated from the ambient air. The instrument may be dried passively by a microbe blocking filter (98) in the container or by using a fan (80) to pump drying air longitudinally through the container.

25 Claims, 2 Drawing Sheets

MEDICAL INSTRUMENT DECONTAMINATION AND STERILIZATION PROCESSOR

The present application is a continuation-in-part of U.S. application Ser. Nos. 681,118, and 349,304, filed Apr. 5, 1991 and May 9, 1989, respectively, application Ser. No. 349,304, issued Feb. 25, 1992 as U.S. Pat. No. 5,091,343, which are continuations-in-part of U.S. application Ser. No. 140,388 filed Jan. 4, 1988 now U.S. Pat. No. 4,892,706 and of application Ser. No. 165,189 filed Mar. 7, 1988 now U.S. Pat. No. 5,037,623, application Ser. Nos. 140,388 and 165,189, in turn, both being continuations-in-part of patent application Ser. No. 826,730, filed Feb. 6, 1986, now U.S. Pat. No. 4,731,222.

BACKGROUND OF THE INVENTION

The present invention pertains to the art of microbial decontamination. It finds particular application in conjunction with sterilizing endoscopes and will be described with particular reference thereto. It is to be appreciated, however, that the invention is also applicable to disinfecting systems as well as decontamination systems for a wide range of items including, medical, dental, laboratory, and manufacturing equipment from which undesirable microbial life forms are to be eliminated.

Disinfection generally connotes an absence or elimination of pathogenic life forms. Sterilization generally connotes the absence or removal of not just endospores. Microbial decontamination is a generic term which encompasses both sterilization and disinfection.

High temperature steam sterilization commonly used for heat resistance instrument is unsuited for instruments continuing heat sensitive rubber and plastic components or adhesives, generally not rubber or plastic such as endoscopes, can be destroyed or have their useful lives severely curtailed by the high temperature and pressures associated with a steam autoclave.

Endoscopes and other more sensitive medical equipment are often sterilized with ethylene oxide, which is thermally less severe than steam. The items must be exposed to the ethylene oxide for a relatively long time, on the order of $3\frac{1}{2}$ hours. Thereafter 8-12 hours are normally required for degassing or desorbing the ethylene oxide from plastic and other ethylene oxide absorptive materials. The pressurization and depressurization cycles of ethylene oxide sterilization may damage lens systems and other delicate instrument components. Moreover, ethylene oxide is relatively expensive. It is sufficiently toxic and volatile that extensive precautions are commonly taken to assure operator safety. Moreover, chloroflurocarbons commonly used to dilate ethylene oxide to make it nonexplosive is an environmental hazard.

Liquid systems are commonly used for disinfecting endoscopes and other heat sensitive and delicate instruments. Using liquid sterilants or disinfectants to achieve disinfection is normally rapid, cost-effective, and does minimal damage to medical devices. Commonly, a technician mixes a sterilant composition and manually immerses the item to be disinfected. The immersion is timed by the technician. Technician variation in the mixing, timing, and equipment handling raises problems of assurance and reproduceability of the manual disinfection process. Rinsing of the items to remove chemical residues also adds a variable that reduces the assurance of disinfection or sterility. Once rinsed, the disinfected endoscope or other item is susceptible to reinfection by airborne microbes.

Liquid systems require complete immersion of the endoscope in liquid solution. Large and bulking items require large immersion containers, hence large volumes of the sterilant or disinfecting solution.

In accordance with the present invention, a new and improved sterilization apparatus, system, and method are provided which overcomes the above-referenced problems and others.

SUMMARY OF THE INVENTION

In accordance with one aspect of the present invention, a liquid microbial decontamination apparatus is provided. A supporting means supports an item to be microbially decontaminated in a decontamination chamber. A spray nozzle means sprays the chamber and the received item with an antimicrobial liquid mist or spray. The spray wets all surfaces of the received item and changes without the chamber becoming filled.

In accordance with one more limited aspect of the present invention, at least one connector means is provided for directing a stream of the antimicrobial liquid through an internal passageway of the item.

In accordance with another aspect of the present invention, a recirculation system is provided. The antimicrobial liquid that is passed through the internal passage or which has dripped off the outer surface of the item is recirculated back to the spray and connector means.

In accordance with another aspect of the present invention, a liquid microbial decontamination apparatus is provided. A storage container surrounds the item to be sterilized. A liquid antimicrobial liquid is introduced into the interior of the container to decontaminate the received item.

After the liquid is drained from the interior of the container, the container and the item are removed as a unit to retain the decontaminated condition. In one embodiment, the container is a flexible sleeve whose ends are closed or sealed to prevent recontamination from airborne contaminants. The storage container may also be a structurally stronger container with quick closing and closure configurations.

In accordance with a more limited aspect of the present invention, a liquid sterilant or disinfectant are sprayed in a droplet or mist form.

In accordance with another aspect of the present invention, the exterior of the storage container is also sprayed with the liquid sterilant or disinfectant.

In accordance with another more limited aspect of the present invention, microbially decontaminated drying air is passed through the storage container to dry the rinse liquid from the sterilized item.

One advantage of the present invention is that it effectively sterilizes or disinfects endoscopes and other delicate instruments.

Another advantage of the present invention is that it sterilizes or disinfects bulky and awkward items with minimal volume of liquid sterilant or disinfectant.

Another advantage of the present invention is that it maintains the sterile or disinfected condition of the item during temporary or longer term storage.

Still further advantages of the present invention will become apparent to those of ordinary skill in the art upon reading and understanding the following description.

BRIEF DESCRIPTION OF THE DRAWINGS

The invention may take form in various parts and arrangements of parts, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
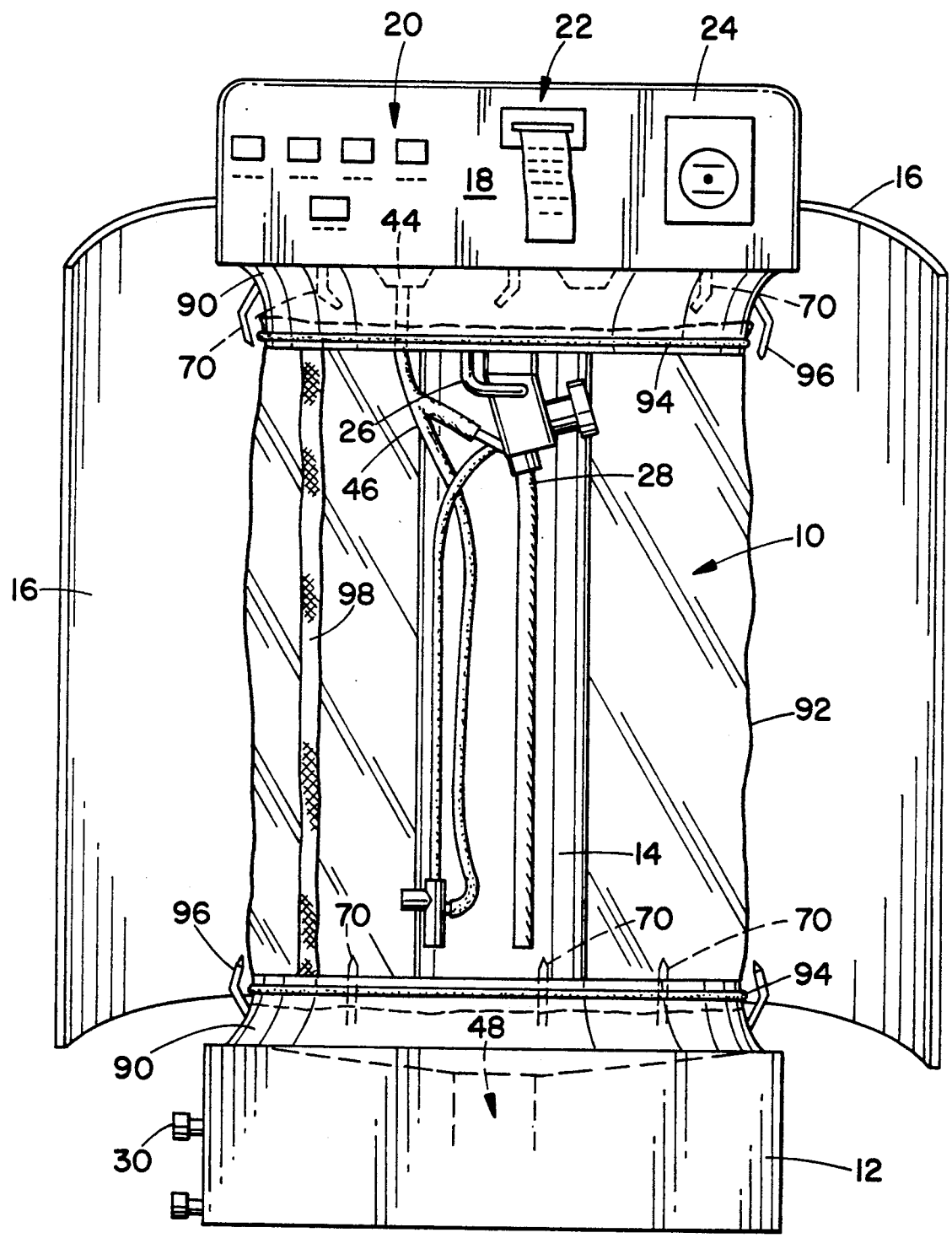
FIG. 1 is an external view of a microbial decontamination apparatus in accordance with the present invention.

With reference to FIG. 1, a microbial decontamination apparatus, preferably a sterilizing apparatus, defines a decontamination or sterilizing chamber 10. More specifically, the decontamination apparatus includes a base portion 12 from which an upstanding structural member 14 extends. Casters or wheels (not shown) permit the apparatus to be repositioned easily. The structural member 14 has an inner face which defines a portion of the rear surface of the decontamination chamber 10 and a hollow interior to permit the passage of appropriate plumbing and electrical lines. A pair of clamshell doors 16 are hingedly connected to either side of the post structural member 14. In the open configuration, the clamshell doors allow easy, ready access to the decontamination chamber. In the closed position, the clamshell doors seal and define the remainder of the decontamination chamber. The clam shell doors close in a fluid tight seal. Optionally the chamber may be completely or partially flooded with a decontaminant, prewash, rinse, and/or other liquids. An upper body portion 18 is mounted at the top of the support member 14.

The upper body portion 18 includes appropriate control buttons 20 for controlling and initiating sterilizing, disinfecting, or other decontamination cycles. A printer 22 prints out pertinent information concerning each sterilization on a paper receipt. For example, the information may include the date and time of the sterilization, the duration of the sterilization cycle, temperature and other processed parameters, an operator identification, and the like. An access port 24 has a chamber for receiving the agents, such as powdered or liquid sterilant or disinfectant forming reagents. A hanger or retainer means 26 extends from the upper housing 18 into the decontamination chamber 10 to support or hang an object 28 to be disinfected. In the preferred embodiment, the structural member 14 supports the upper body portion 18 about 2 meters above the lower base portion 12 in order to accommodate the full length of an endoscope 28.

Figure 2:
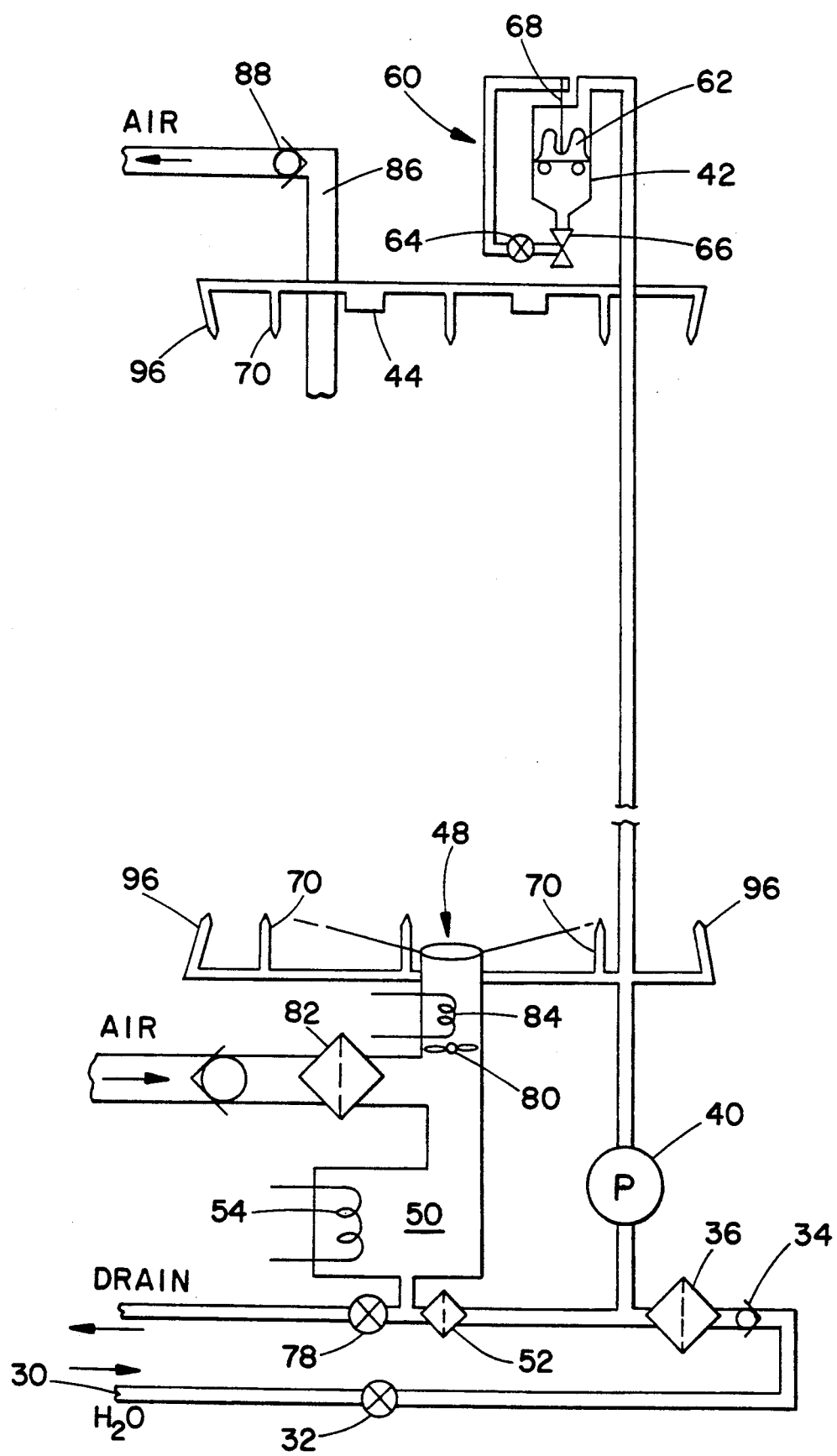
FIG. 2 is a diagrammatic illustration of the fluid handling paths of the apparatus of FIG. 1.

With continuing reference to FIG. 1 and further reference to FIG. 2, water received at a water inlet 30 is conveyed through a control valve 32 and a check valve 34 to a disinfecting or sterilizing means 36. In the preferred embodiment, the disinfecting or the sterilizing means is a filter which mechanically separates microbes and other contaminants from received water. Other techniques for microbially decontaminating the rinse are also contemplated, such as heat, a dedicated fluid supply, and the like.

A pump means 40 pumps the received water through a reagent mixing region 42 disposed behind access port 24. The water flows through the mixing chamber 42 dissolving powdered reagents, such as wetting agents, surfactants, and corrosion inhibitors deposited in the mixing chamber. The water with the dissolved reagents flows across the sterilizing means 36 to a series of connectors 44 such that all surfaces downstream from the sterile rinse source are microbially decontaminated. A manifold or tubing assembly 46 channels the fluid from the mixing region to one or more of the connectors through internal passages of the endoscope 28. The liquid falls by gravity to a lower surface of the decontamination chamber 10 and out a drain 48.

The liquid from the drain collects in a reservoir 50 which is interconnected through a filter 52 to the pump 40. A heating element 72 is provided for adjusting the temperature of the sterilant or decontamination liquid. In this manner, the pump recirculates the fluid. The drain 48 may optionally be closed to create an immersion portion in the cycle.

In the illustrated embodiment, a siphon assembly 60 is selectively actuated to puncture a liquid sterilant containing ampule 62 and intermix the sterilant with the circulating liquid. A valve 64 is opened a short time after the circulation of fluid has started. A ventury 66 causes an ampule puncturing needle 68 to withdraw the liquid sterilant from the ampule. In another embodiment, a powdered reagent for forming the disinfecting or sterilizing solution is contained in the ampule which is cut or opened at the appropriate point in the cycle. In other embodiments, a powdered sterilant may be intermixed with the powdered reagents, deposited into the bottom of the mixing region, and dissolved concurrently therewith, also eliminating the siphon assembly.

The sterilant or antimicrobial composition containing liquid is conveyed to a plurality of spray nozzles 70. The filter 52 is selected to be sufficiently fine to move any particulates which might clog or interfere with the appropriate operation of the spray nozzles. Various types of spray nozzles are contemplated. In one embodiment, the spray nozzles are ultrasonic misting or fogging nozzles. An electroacoustic transducer is mounted in each nozzle to eject ultrasonically a mist of fine droplets. In this manner, a mist is created in the decontamination chamber which settles on and coats the surface of the item to be sterilized. In another embodiment, the spray nozzles receive motive power from the pump 40, or a supplemental pump, to spray a stream of spray of liquid against the item to be sterilized. Various other spray nozzles or combinations thereof are also contemplated. For example, higher powered spray nozzles may be used at the beginning of the cycle and during the rinse with the ultrasonic misting nozzle used in television.

By misting or spraying droplets of antimicrobial reagent, a relatively small volume of liquid may be utilized. For example, effective sterilization can be carried out in a decontamination chamber of about 90 liters with only a few liters of sterilant.

At the end of the sterilization, disinfection, or other microbial decontamination cycle, a drain valve 78 is opened to drain the spent antimicrobial liquid. The valve 78 is then closed and valve 32 is opened such that additional water sterilized by the sterilizing means 36 is introduced into the system and circulated by pump 40 to rinse reagent residue from the sterilized or decontaminated item. It will be noted that all tubing and surfaces over which the rinse water flows downstream from the sterilizing means 36 through the spray nozzles and connectors are sterilized by contact with the circulating liquid sterilant prior to the rinse step.

Optionally, the sterilized and rinsed items may also be dried. An air circulating means or fan 80 draws air through an air decontaminating or sterilizing means 82, such as a filter that mechanically separates microbes from the incoming air. The sterilized air is blown over a heating element 84 to adjust the temperature of the drying air. An exhaust vent 86 through a one way check valve 88 is provided to enable the moisture laden drying air to escape from the decontamination chamber. Preferably, the drying air supply assembly is mounted in the lower surface of the decontamination chamber such that the liquid sterilant flows therethrough to the reservoir 50 assuring that all parts of the drying system are sterilized. Optionally, a spray nozzle is mounted in the exhaust vent 86 to sterilize the surfaces thereof.

It is to be appreciated, that the endoscope or sterilized item will not always be used immediately. To this end, a storage container is received in the chamber 20 around the item. Closable ends of the storage container are open to permit free flow of the antimicrobial mist, drying air, and rinse fluids. In the illustrated embodiment, matching retainer rings 90 are mounted to the top and bottom cabinet portions, each having a diameter smaller than the inner diameter of the clamshell doors 16. The storage container includes a transparent, flexible plastic sleeve 92 whose lower end is secured to a lower one of the retaining rings 90. The sleeve may have a built-in elastomeric material, be surrounded by a rubber retainer band 94, or other appropriate anchoring mechanisms may be provided. For example, the ends of the sleeve or bag may be contracted with a drawstring, an embedded elastomer, or the like. The seal between the retaining rings 90 and the plastic sleeve 92 need not be interconnected liquid tight.

After the sleeve is secured to the over retainer ring, the endoscope 28 or other item to be sterilized is hung on the hook 26. The sleeve is raised and its upper end is attached to the upper retaining ring. The sterilization, rinse, and drying sequence described above is then performed. In order to assure sterility, external spray nozzles or jets 96 are provided around the exterior of the sleeve to sterilize its exterior. Analogously, drain apertures are provided for draining the externally sprayed liquid to the reservoir 50. After the cycle is completed, the operator opens the doors 16 and removes the sleeve and enclosed endoscope as a unit. That is, the operator supports the endoscope by grasping the exterior of the bag or sleeve such that the sleeve prevents contamination from the operator's hands from reaching the endoscope. After the ends of the bag are removed from the retainer rings, the ends are closed or sealed. For example, the bag may be folded over and secured with tape. The receipt printed by printer 22 is commonly taped to the bag to remain with the sterilized item until utilized.

Other storage containers can also be used. For example, each container may hold one of plural sterilized items. The container may, for example, be a rigid, or semirigid rectangular cross section sleeve for easy stacking and storage. The ends of the container have a quick seal closure, such as a folding over construction or flap, twist close apertures, a hinged lid, a cover of different construction, such as thin film that is taped or drawn closed, and the like.

Rather than actively drying the item with forced air, the endoscope or other sterilized item can be dried passively. In order to achieve the passive drying, the plastic sleeve is provided with a drying strip 98. The drying strip is an air and water vapor permeable, microbe impermeable filter material which permits trapped water and water vapor to escape from the interior of the plastic sleeve 92.

The invention has been described with reference to the preferred embodiment. Obviously, modifications and alterations will occur to those skilled int he art. It is intended that the invention be construed as including all such alterations and modifications which come within the scope of the appended claims or the equivalents thereof.

Having thus described the preferred embodiment, the invention is now claimed to be:

1. A microbial decontamination apparatus comprising:
   a selectively accessible decontamination chamber including:
      a fixed base portion,
      a vertically elongated back portion attached to and extending upward from the base portion,
      a top portion mounted on the back portion
      a pair of front doors hingedly connected to the back portion for selectively sealing an interior of the chamber in a closed configuration and providing access to the chamber interior in a open configuration;
   a means disposed adjacent the top portion for hanging an elongated item to be microbially decontaminated completely within the decontamination chamber;
   a spray nozzle means for spraying the hanging item and the interior of the chamber;
   an antimicrobial solution supply means for supplying an antimicrobial solution to the spray nozzle means such that the item and the chamber interior are microbially decontaminated;
   a drain means for draining accumulated liquid from a bottom of the decontamination chamber such that the antimicrobial solution is removed from the decontamination chamber without the chamber becoming filled.

2. The apparatus as set forth in claim 1 wherein the item has at least one internal passage and further including a connecting means for selectively connecting the internal passage of the item to the antimicrobial solution supply means.

3. A microbial decontamination apparatus comprising:
   a means for defining a selectively accessible, vertically elongated decontamination chamber;
   a means for hanging an elongated item to be microbially decontaminated in the decontamination chamber;
   a flexible sleeve which is secured adjacent upper and lower portions of the decontamination chamber surrounding the elongated item to be decontaminated;
   a spray nozzle means disposed inside the sleeve for spraying the hanging elongated item;
   an antimicrobial solution supply means for supplying an antimicrobial solution to the spray nozzle means such that an interior of the sleeve and the elongated item are microbially decontaminated;
   a drain means for draining accumulated liquid from a bottom of the decontamination chamber such that the antimicrobial solution is removed from the decontamination chamber without the chamber becoming filled.

4. The apparatus as set forth in claim 3 wherein the spray nozzle means further includes an exterior nozzle means disposed inside the decontamination chamber and outside the sleeve for spraying the antimicrobial solution on an exterior of the sleeve.

5. A microbial decontamination apparatus comprising:
- a means for defining a selectively accessible decontamination chamber;
- a means for supporting an item to be microbially decontaminated in the decontamination chamber;
- a storage container which is removably secured in the decontamination chamber surrounding the item to be decontaminated, at least a portion of the container being constructed of a filter material which is sufficiently porous to permit air and water vapor to pass and sufficiently fine to prevent microbes from entering the container;
- a spray nozzle means disposed to spray inside the container and the item such that an interior of the container and the item are sprayed;
- an antimicrobial solution supply means for supplying an antimicrobial solution to the spray nozzle means;
- a drain means for draining accumulated liquid from a bottom of the decontamination chamber such that the antimicrobial solution is removed from the decontamination chamber without the chamber becoming filled.

6. A microbial decontamination apparatus comprising:
- a means for defining a selectively accessible decontamination chamber;
- a means for supporting an item to be microbially decontaminated in the decontamination chamber, the item having an internal passage;
- a spray nozzle means for spraying an exterior of the supported item;
- a connecting means for selective interconnection with the item internal passage;
- an antimicrobial solution supply means for supplying an antimicrobial solution;
- a drain means for draining accumulated liquid from a bottom of the decontamination chamber;
- a pump means for pumping liquid received in the drain means to the spray nozzle means and the connecting means such that the antimicrobial solution is recirculated.

7. The apparatus as set forth in claim 6 wherein the decontamination chamber is vertically elongated and the supporting means includes means for hanging an elongated item to be microbially decontaminated.

8. The apparatus as set forth in claim 6 further including a storage container which is removably secured in the decontamination chamber surrounding the item to be decontaminated, the spray nozzle means being disposed to spray inside the container such that an interior of the container and the item are sprayed.

9. The apparatus as set forth in claim 6 further including a drain valve means for selectively draining the antimicrobial solution and further including a source of microbially decontaminated rinse operatively connected with the pump means for supplying the rinse to the pump for rinsing the microbially decontaminated item.

10. The apparatus as set forth in claim 6 further including a mixing region for receiving a sterilant concentrated, the pump means being connected with the mixing region for pumping water therethrough to mix the antimicrobial solution.

11. A microbial decontamination apparatus comprising:
- an upper retainer structure;
- a lower retainer structure;
- a hanging means supported by the upper retainer structure for hanging an article to be microbially decontaminated between the upper and lower supporting structures;
- a flexible sleeve removably attached between the upper and lower supporting structures and surrounding the article to be microbially decontaminated, such that after the microbial decontamination, the flexible sleeve is detachable from the upper and lower supporting structures after microbial decontamination and securable to the article such that the microbially decontaminated article and secured sleeve can be removed as a unit with the decontaminated article enclosed within the flexible sleeve to maintain microbially decontamination;
- a nozzle affixedly mounted to the upper retainer structure for introducing an antimicrobial agent into contact with the article inside the flexible sleeve, the nozzle remaining fixed to the upper retainer structure when the flexible sleeve and the article are removed.

12. The apparatus as set forth in claim 11 wherein the flexible sleeve includes at least a portion constructed of a filter material which is sufficiently porous to permit air and water vapor to pass and sufficiently fine to prevent microbes from entering the sleeve.

13. A sterilizing or disinfecting apparatus comprising:
- a elongated decontamination chamber defined between upper and lower housing portions;
- at least one elongated door for providing access to the decontamination chamber;
- a support means operatively connected with the upper housing portion for supporting an instrument in the decontamination chamber;
- a container surrounding the hanging instrument and spaced therefrom, the container being supported by the upper and lower housing portions;
- a fluid outlet disposed in the upper housing portion;
- a connecting means for connecting the fluid outlet with at least one interior passage of the instrument;
- at least one spray nozzle mounted to at least one of the upper and lower housing portions for spraying the instrument;
- a means for supplying a sterilant or disinfectant solution to the spray nozzle and fluid outlet means such that the solution flows through the internal passage and sprays the exterior of the instrument;
- a drain means for collecting the solution which drains by gravity from the instrument without the instrument becoming immersed in the solution.

14. The apparatus as set forth in claim 13 further including a pump means for pumping liquid collected in the drain means to the spray nozzle and the fluid outlet such that the solution is recirculated.

15. The apparatus as set forth in claim 14 further including;
- a means for microbially decontaminating ambient air;

a means for blowing the microbially decontaminated air through the interior of the container to dry the instrument.

16. The apparatus as set forth in claim 13 further including a drain valve means for selectively draining the solution and further including a source of microbially decontaminated rinse water operatively connected with the pump means for supplying the rinse water to the pump means to be selectively pumped to the spray nozzle and fluid outlet for rinsing the instrument.

17. The apparatus as set forth in claim 16 further including a mixing region for receiving a sterilant or disinfectant concentrate in either liquid or dry form, the mixing region being connected with the pumping means to mix the solution as the pump means pumps water from a water source therethrough.

18. A method of microbially decontaminating an elongated item, the method comprising:
    hanging the item in a microbial decontamination chamber;
    placing a flexible plastic sleeve which is open at both ends around the elongated item;
    spraying an anti-microbial solution on the item and an interior of the flexible sleeve;
    draining the anti-microbial solution from the sleeve and the item;
    terminating spraying of the anti-microbial solution and securing the ends of the flexible plastic sleeve closed with the item therein;
    removing the item and secured flexible plastic sleeve from the decontamination chamber.

19. The method as set forth in claim 18 wherein the spraying step includes spraying an ultrasonic mist into the sleeve.

20. The method as set forth in claim 18 wherein anti-microbial solution that drains from the item and the sleeve is collected and recirculated to be sprayed again on the item and the interior of the sleeve.

21. The method as set forth in claim 18 further including before the step of removing the elongated item and secured flexible plastic sleeve from the decontamination chamber, blowing microbially decontaminated air through the sleeve to dry the item and the sleeve interior.

22. A method of microbially decontaminating an elongated item which has an internal passage, the method comprising:
    hanging the elongated item completely within a microbial decontamination chamber adjacent a plurality of spray nozzles and with the internal passage in fluid communication with an outlet connector;
    spraying the item exterior with an anti-microbial solution from the spray nozzles and flushing the internal passage with an anti-microbial solution from the outlet connector;
    draining the anti-microbial solution from the item;
    recirculating the anti-microbial solution by collecting the anti-microbial solution drained from the item, pumping the anti-microbial solution to the spray nozzle and the outlet connector;
    continuing the recirculating of the anti-microbial solution until the item is at least disinfected;
    draining the anti-microbial solution from the microbial decontamination chamber;
    rinsing the elongated item and its internal passage with a microbially decontaminated rinse fluid;
    draining the microbially decontaminated rinse fluid from the item and the microbial decontamination chamber;
    removing the elongated item from the decontamination chamber.

23. The method as set forth in claim 22 further including before the step of removing the elongated item from the chamber, blowing microbially decontaminated air through the chamber over the item to dry the item.

24. The method as set forth in claim 22 wherein in the spraying step, a fine mist is formed.

25. The method as set forth in claim 22 further including before the spraying step, disposing a storage container which is open at its ends around the elongated item and after the rinsing step, closing the container against airborne microbes.

* * * * *